(12) United States Patent
Obaidi (10) Patent No.: US 11,931,127 B1
(45) Date of Patent: Mar. 19, 2024

(54) MONITORING USERS BIOLOGICAL INDICATORS USING A 5G TELECOMMUNICATION NETWORK

(71) Applicant: T-Mobile USA, Inc., Bellevue, WA (US)

(72) Inventor: Ahmad Arash Obaidi, Issaquah, WA (US)

(73) Assignee: T-Mobile USA, Inc., Bellevue, WA (US)

( * ) Notice: Subject to any disclaimer, the term of this patent is extended or adjusted under 35 U.S.C. 154(b) by 443 days.

(21) Appl. No.: 17/225,972

(22) Filed: Apr. 8, 2021

(51) Int. Cl.
*A61B 5/00* (2006.01)
*A61B 5/11* (2006.01)
*H04W 4/38* (2018.01)

(52) U.S. Cl.
CPC .......... *A61B 5/0022* (2013.01); *A61B 5/0033* (2013.01); *A61B 5/11* (2013.01); *H04W 4/38* (2018.02); *A61B 5/4058* (2013.01); *A61B 5/45* (2013.01)

(58) Field of Classification Search
CPC ....... A61B 5/0022; A61B 5/0033; A61B 5/11; A61B 5/4058; A61B 5/45; H04W 4/38
USPC ...................................................... 340/539.1
See application file for complete search history.

(56) References Cited

U.S. PATENT DOCUMENTS

| | | | |
|---|---|---|---|
| 8,571,890 B2 | 10/2013 | Kalamas | |
| 9,521,202 B2 | 12/2016 | Hwang | |
| 9,623,330 B2 | 4/2017 | Yoshizawa et al. | |
| 9,808,205 B2 | 11/2017 | Koyama et al. | |
| 10,022,051 B2 | 7/2018 | Nakayama et al. | |
| 10,123,199 B2 | 11/2018 | Truong et al. | |
| 10,146,909 B2 | 12/2018 | Dimov et al. | |
| 10,231,652 B2 | 3/2019 | Mauro | |
| 10,263,989 B2 | 4/2019 | Hwang | |
| 10,319,477 B1 | 6/2019 | Bill | |
| 10,409,665 B2 | 9/2019 | Steiner et al. | |
| 10,482,158 B2 | 11/2019 | Yang et al. | |
| 10,617,350 B2 | 4/2020 | Ehrhart et al. | |
| 2008/0294019 A1* | 11/2008 | Tran | G16H 40/63 600/301 |
| 2010/0049074 A1 | 2/2010 | Cortenraad | |
| 2010/0249494 A1 | 9/2010 | Yoshizawa et al. | |
| 2011/0320131 A1 | 12/2011 | Hibino et al. | |
| 2013/0275894 A1 | 10/2013 | Bell et al. | |

(Continued)

*Primary Examiner* — Omar Casillashernandez
(74) *Attorney, Agent, or Firm* — Perkins Coie LLP (57) ABSTRACT

The disclosed system enables monitoring of user's biological indicators for signs of impairment or disease. The system obtains a permission from a user to access a biological indicator. The system obtains a history of the biological indicator associated with the user, where the biological indicator includes movement associated with the user, a voice associated with the user, or an appearance associated with the user. The system obtains a symptom indicating an undesirable state of the user, where the symptom includes a musculoskeletal affliction. The system monitors the biological indicator of user. The system detects an anomaly in the biological indicator by comparing the biological indicator with the history of the biological indicator. The system determines whether the anomaly indicates the undesirable state of the user. Upon determining that the anomaly indicates the undesirable state of the user, the system provides a notification.

20 Claims, 5 Drawing Sheets

(56) References Cited

U.S. PATENT DOCUMENTS

| | | | |
|---|---|---|---|
| 2015/0006028 A1* | 1/2015 | Strauss | B60W 60/0051 |
| | | | 701/36 |
| 2015/0067021 A1* | 3/2015 | Protas | H04L 67/10 |
| | | | 709/202 |
| 2015/0157206 A1 | 6/2015 | Nakayama et al. | |
| 2016/0058394 A1 | 3/2016 | Koyama et al. | |
| 2017/0071531 A1 | 3/2017 | Ehrhart et al. | |
| 2017/0078295 A1 | 3/2017 | Hwang | |
| 2017/0319148 A1* | 11/2017 | Shahin | A61B 5/02055 |
| 2018/0018899 A1 | 1/2018 | Okumura et al. | |
| 2018/0060536 A1 | 3/2018 | Kaneko et al. | |
| 2018/0153477 A1* | 6/2018 | Nagale | A61B 5/021 |
| 2018/0285320 A1 | 10/2018 | Yang et al. | |
| 2018/0293350 A1 | 10/2018 | Dimov et al. | |
| 2018/0303423 A1 | 10/2018 | Mauro et al. | |
| 2018/0358125 A1 | 12/2018 | Bagaev et al. | |
| 2018/0374567 A1 | 12/2018 | Toumazou et al. | |
| 2019/0046486 A1* | 2/2019 | De Rienzo | A61K 31/198 |
| 2019/0057197 A1 | 2/2019 | Wang et al. | |
| 2019/0103128 A1 | 4/2019 | Maekawa | |
| 2020/0288295 A1* | 9/2020 | Martin | H04M 3/5116 |
| 2020/0375544 A1* | 12/2020 | Naveh | A61B 5/112 |
| 2021/0093231 A1* | 4/2021 | Uribe | A61B 5/11 |
| 2021/0345925 A1* | 11/2021 | Davis | A61B 5/7435 |
| 2022/0306187 A1* | 9/2022 | Ojima | B60W 60/0051 |

* cited by examiner

MONITORING USERS BIOLOGICAL INDICATORS USING A 5G TELECOMMUNICATION NETWORK

BACKGROUND

If certain fatal diseases, such as a stroke, are diagnosed in time, permanent impairment to the sufferer can be avoided. Stroke is the fourth leading cause of death in the United States. Strokes result in death 17 percent of the time. In other words, one-in-six strokes are fatal. The remaining five-in-six strokes are nonfatal but can cause permanent weakness, visual loss, language and other cognitive deficits, and other impairments. For example, if stroke is anticipated in time, the patient can receive a nitroglycerin pill which reduces the patient's blood pressure. Lowering blood pressure reduces the risk of stroke. Epidemiological studies have shown that for each 10 mm Hg lower systolic blood pressure, there is a decrease in risk of stroke of approximately one third in persons aged 60 to 79 years.

BRIEF DESCRIPTION OF THE DRAWINGS

Detailed descriptions of implementations of the present invention will be described and explained through the use of the accompanying drawings.

The technologies described herein will become more apparent to those skilled in the art from studying the Detailed Description in conjunction with the drawings. Embodiments or implementations describing aspects of the invention are illustrated by way of example, and the same references can indicate similar elements. While the drawings depict various implementations for the purpose of illustration, those skilled in the art will recognize that alternative implementations can be employed without departing from the principles of the present technologies. Accordingly, while specific implementations are shown in the drawings, the technology is amenable to various modifications.

DETAILED DESCRIPTION

The disclosed system and method enable monitoring users' biological indicators, such as users' voice, users' appearance, blood pressure, weight, complexion, breath, urine, etc. for signs of impairment or disease, such as a stroke or diabetes. Initially, the system obtains permission from a user to access a biological indicator, by having the user opt-in to use the system. The system obtains a history of the biological indicator associated with the user, through accessing the user's public information such as social media posts, and/or the user's private information, such as records of doctors' visits, user's prescriptions, etc. The system can obtain multiple symptoms associated with a stroke, such as a loss of balance, slurred speech, and an affliction of facial muscles from a medical database such as CDC database. The system can monitor, using a 5G telecommunication network or a higher generation telecommunication network, the biological indicator associated with the user. The monitoring of the biological indicator can require a bandwidth of a 5G telecommunication network or the higher generation telecommunication network because of the high volume of data, such as a video of the user, that needs to be transmitted between the user equipment (UE) and a cloud server. The 5G telecommunication network is beneficial because of low latency, high bandwidth throughput and 2-way near real-time data communication with sensors and AI elements that can evaluate a patient and provide the necessary feedback.

The system can detect an anomaly in the biological indicator by comparing the biological indicator with the history of the biological indicator to detect whether the user's speech currently is more slurred than usual, whether the user's facial muscles are more afflicted than usual, whether the user may have fallen, and/or to determine any changes in the user's balance. The system can determine whether the anomaly indicates one or more symptoms among the multiple symptoms of a stroke. Upon determining that the anomaly indicates one or more symptoms among the multiple symptoms of the stroke, the system can provide a notification to the user, to a family member, or to an emergency responder, that the user is experiencing the stroke. Similarly, if the user is diabetic, the system can similarly notify third parties if the user's blood sugar levels are outside a set range.

The description and associated drawings are illustrative examples and are not to be construed as limiting. This disclosure provides certain details for a thorough understanding and enabling description of these examples. One skilled in the relevant technology will understand, however, that the invention can be practiced without many of these details. Likewise, one skilled in the relevant technology will understand that the invention can include well-known structures or features that are not shown or described in detail, to avoid unnecessarily obscuring the descriptions of examples.

Wireless Communications System

Figure 1:
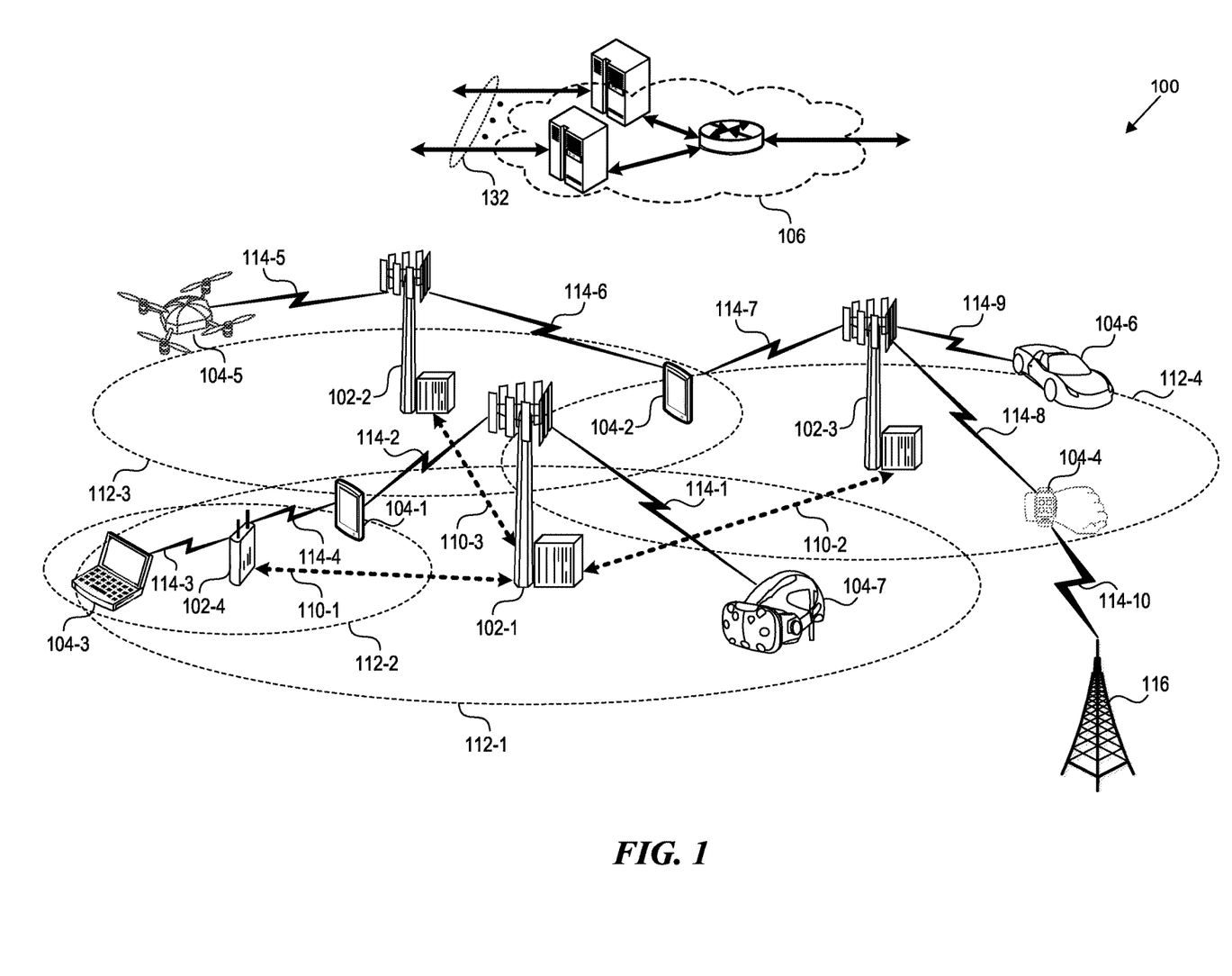
FIG. 1 is a block diagram that illustrates a wireless communications system.

FIG. 1 is a block diagram that illustrates a wireless telecommunication system 100 ("system 100") in which aspects of the disclosed technology are incorporated. The system 100 includes base stations 102-1 through 102-4 (also referred to individually as "base station 102" or collectively as "base stations 102"). A base station is a type of network access node (NAN) that can also be referred to as a cell site, a base transceiver station, or a radio base station. The system 100 can include any combination of NANs including an access point, radio transceiver, gNodeB (gNB), NodeB, eNodeB (eNB), Home NodeB or eNodeB, or the like. In addition to being a WWAN base station, a NAN can be a WLAN access point, such as an Institute of Electrical and Electronics Engineers (IEEE) 802.11 access point.

The NANs of a network formed by the system 100 also include wireless devices 104-1 through 104-8 (referred to individually as "wireless device 104" or collectively as "wireless devices 104") and a core network 106. The wireless devices 104-1 through 104-8 can correspond to or include network entities capable of communication using various connectivity standards. For example, a 5G communication channel can use millimeter wave (mmW) access frequencies of 28 GHz or more. In some implementations, the wireless device 104 can operatively couple to a base station 102 over an LTE/LTE-A communication channel, which is referred to as a 4G communication channel.

The core network 106 provides, manages, and controls security services, user authentication, access authorization, tracking, Internet Protocol (IP) connectivity, and other access, routing, or mobility functions. The base stations 102 interface with the core network 106 through a first set of backhaul links 108 (e.g., S1 interfaces) and can perform radio configuration and scheduling for communication with the wireless devices 104 or can operate under the control of a base station controller (not shown). In some examples, the base stations 102 can communicate, either directly or indirectly (e.g., through the core network 106), with each other over a second set of backhaul links 110-1 through 110-3 (e.g., X1 interfaces), which can be wired or wireless communication links.

The base stations 102 can wirelessly communicate with the wireless devices 104 via one or more base station antennas. The cell sites can provide communication coverage for geographic coverage areas 112-1 through 112-4 (also referred to individually as "coverage area 112" or collectively as "coverage areas 112"). The geographic coverage area 112 for a base station 102 can be divided into sectors making up only a portion of the coverage area (not shown). The system 100 can include base stations of different types (e.g., macro and/or small cell base stations). In some implementations, there can be overlapping geographic coverage areas 112 for different service environments (e.g., Internet-of-Things (IoT), mobile broadband (MBB), vehicle-to-everything (V2X), vehicle-to infrastructure (VTI), machine-to-machine (M2M), machine-to-everything (M2X), ultra-reliable low-latency communication (URLLC), machine-type communication (MTC)), etc.

The system 100 can include a 5G network and/or an LTE/LTE-A or other network. In an LTE/LTE-A network, the term eNB is used to describe the base stations 102 and in 5G new radio (NR) networks, the term gNBs is used to describe the base stations 102 that can include mmW communications. The system 100 can thus form a heterogeneous network in which different types of base stations provide coverage for various geographical regions. For example, each base station 102 can provide communication coverage for a macro cell, a small cell, and/or other types of cells. As used herein, the term "cell" can relate to a base station, a carrier or component carrier associated with the base station, or a coverage area (e.g., sector) of a carrier or base station, depending on context.

A macro cell generally covers a relatively large geographic area (e.g., several kilometers in radius) and can allow access by wireless devices with service subscriptions with a wireless network service provider. As indicated earlier, a small cell is a lower-powered base station, as compared with a macro cell, and can operate in the same or different (e.g., licensed, unlicensed) frequency bands as macro cells. Examples of small cells include pico cells, femto cells, and micro cells. In general, a pico cell can cover a relatively smaller geographic area and can allow unrestricted access by wireless devices with service subscriptions with the network provider. A femto cell covers a relatively smaller geographic area (e.g., a home) and can provide restricted access by wireless devices having an association with the femto cell (e.g., wireless devices in a closed subscriber group (CSG), wireless devices for users in the home). A base station can support one or multiple (e.g., two, three, four, and the like) cells (e.g., component carriers). All fixed transceivers noted herein that can provide access to the network are NANs, including small cells.

The communication networks that accommodate various disclosed examples can be packet-based networks that operate according to a layered protocol stack. In the user plane, communications at the bearer or Packet Data Convergence Protocol (PDCP) layer can be IP-based. A Radio Link Control (RLC) layer then performs packet segmentation and reassembly to communicate over logical channels. A Medium Access Control (MAC) layer can perform priority handling and multiplexing of logical channels into transport channels. The MAC layer can also use Hybrid ARQ (HARQ) to provide retransmission at the MAC layer, to improve link efficiency. In the control plane, the Radio Resource Control (RRC) protocol layer provides establishment, configuration, and maintenance of an RRC connection between a wireless device 104 and the base stations 102 or core network 106 supporting radio bearers for the user plane data. At the Physical (PHY) layer, the transport channels are mapped to physical channels.

As illustrated, the wireless devices 104 are distributed throughout the system 100, where each wireless device 104 can be stationary or mobile. A wireless device can be referred to as a mobile station, a subscriber station, a mobile unit, a subscriber unit, a wireless unit, a remote unit, a handheld mobile device, a remote device, a mobile subscriber station, an access terminal, a mobile terminal, a wireless terminal, a remote terminal, a handset, a mobile client, a client, or the like. Examples of a wireless device include user equipment (UE) such as a mobile phone, a personal digital assistant (PDA), a wireless modem, a handheld mobile device (e.g., wireless devices 104-1 and 104-2), a tablet computer, a laptop computer (e.g., wireless device 104-3), a wearable (e.g., wireless device 104-4). A wireless device can be included in another device such as, for example, a drone (e.g., wireless device 104-5), a vehicle (e.g., wireless device 104-6), an augmented reality/virtual reality (AR/VR) device such as a head-mounted display device (e.g., wireless device 104-7), an IoT device such as an appliance in a home (e.g., wireless device 104-8), a portable gaming console, or a wirelessly connected sensor that provides data to a remote server over a network.

A wireless device can communicate with various types of base stations and network equipment at the edge of a network including macro eNBs/gNBs, small cell eNBs/gNBs, relay base stations, and the like. A wireless device can also communicate with other wireless devices either within or outside the same coverage area of a base station via device-to-device (D2D) communications.

The communication links 114-1 through 114-11 (also referred to individually as "communication link 114" or collectively as "communication links 114") shown in system 100 include uplink (UL) transmissions from a wireless device 104 to a base station 102, and/or downlink (DL) transmissions, from a base station 102 to a wireless device 104. The downlink transmissions can also be called forward link transmissions while the uplink transmissions can also be called reverse link transmissions. Each communication link 114 includes one or more carriers, where each carrier can be a signal composed of multiple sub-carriers (e.g., waveform signals of different frequencies) modulated according to the various radio technologies. Each modulated signal can be sent on a different sub-carrier and carry control information (e.g., reference signals, control channels), overhead information, user data, etc. The communication links 114 can transmit bidirectional communications using FDD (e.g., using paired spectrum resources) or TDD operation (e.g., using unpaired spectrum resources). In some implementations, the communication links 114 include LTE and/or mmW communication links.

In some implementations of the system 100, the base stations 102 and/or the wireless devices 104 include multiple antennas for employing antenna diversity schemes to improve communication quality and reliability between base stations 102 and wireless devices 104. Additionally or alternatively, the base stations 102 and/or the wireless devices 104 can employ multiple-input, multiple-output (MIMO) techniques that can take advantage of multi-path environments to transmit multiple spatial layers carrying the same or different coded data.

System 100 can be used to transmit data gathered by various sensors, described in this application, to a remote server for further analysis. When the system 100 employs 5G or a higher generation technology standard for broadband cellular networks, the data gathered by various sensors can be continuously transmitted to the server because the 5G or higher networks have high throughput bandwidth. For example, the 5G network can support the continuous transmission of video from a camera. When the system employs 4G or lower generation technology, the sensor data can be transmitted at predetermined intervals, such as periodically, to obtain occasional measurements of a biological indicator associated with the user.

Monitoring User's Biological Indicators

Figure 2:
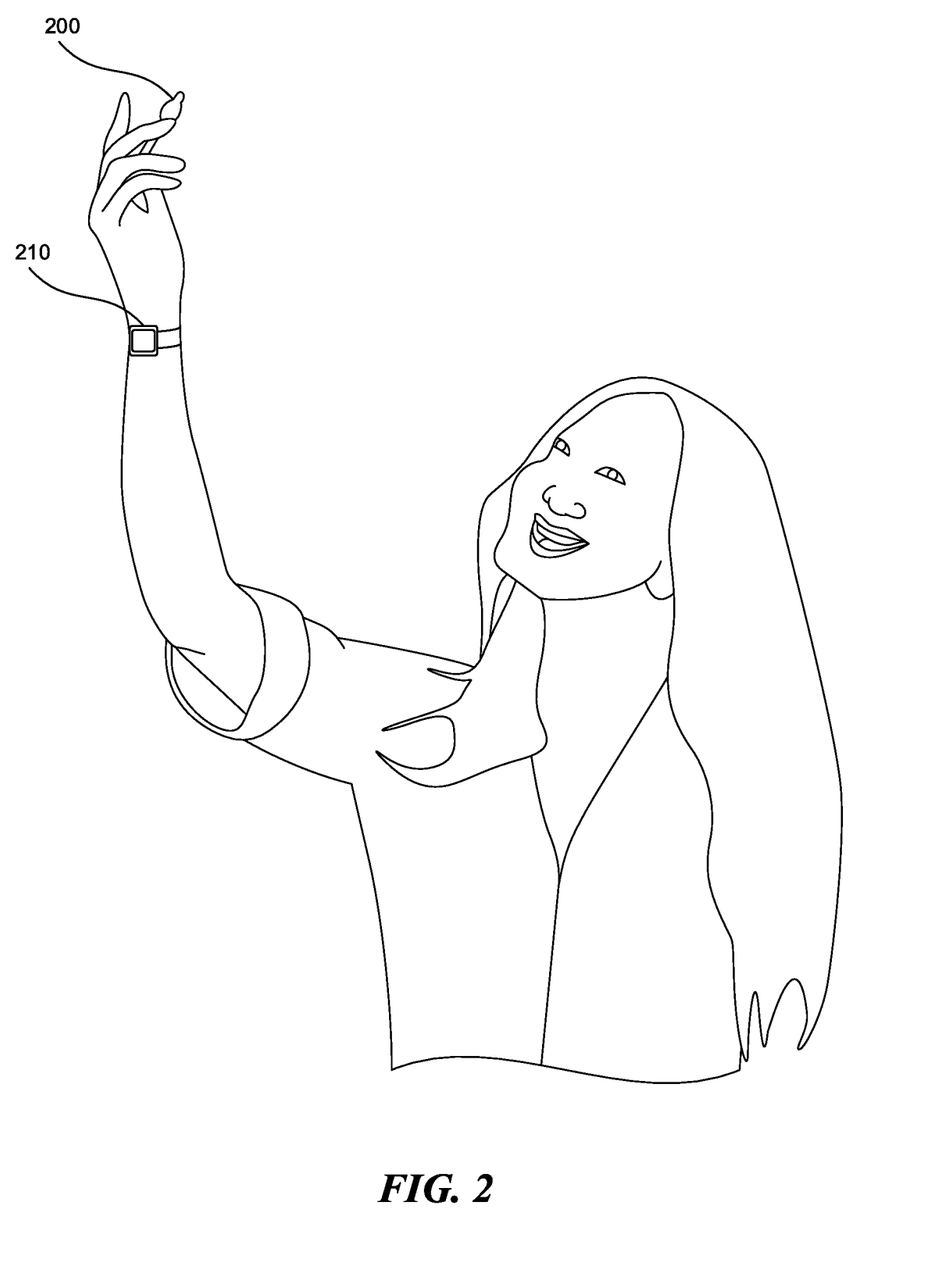
FIG. 2 shows various sensors that can be used to monitor the user.

FIG. 2 shows various sensors that can be used to monitor the user. A user can have various UEs 200, 210, for example, devices such as a mobile device, a tablet, a scale, a device for measuring blood pressure or blood sugar levels, a vehicle, a wearable device such as a watch, glasses, earbuds, etc. Each of the devices 200, 210 can have sensors such as accelerometers, GPS, breath analyzers, heart rate, blood oxygen levels, etc., that can measure various biological indicators of the user. The devices 200, 210 can be Internet of Things (IOT) devices connected to the Internet.

For example, a scale weighing the user can provide the measurements to a central processor for storing and analysis. In another example, a urine analysis device can be installed in the toilet and can measure the contents of urine to detect biological indicators such as blood sugar, blood, viruses, and/or bacteria contained in the urine. Based on the measurements, the urine analysis device can determine whether the user is prediabetic, has a urinary tract infection, has COVID-19, etc. The wearable device 210 can measure biological indicators such as heartbeats per minute and/or blood pressure. The devices 200, 210 can also measure biological indicators including user's weight, user's movement, speed of walking, user's appearance using video or images, pain level, and/or user's voice.

In a third example, a workout machine, such as a treadmill, can be Wi-Fi enabled and can be an IOT device. The workout machine can record how frequently the user works out and the user's pulse during the workout. Based on the pulse, a processor connected to the workout machine can determine whether the user is at risk of a cardiac event or a stroke. The processor can warn the user of the risk.

In a fourth example, an accelerometer in a user's watch 210 can measure the user's balance and orientation. If the user falls down, and remains lying on the floor, the accelerometer in the UE 210 can detect the sudden change in orientation, and the prolonged horizontal orientation, and can cause an alert to be sent to 911 or family members, and/or can notify the user through an alarm or a text to personally call 911.

A processor associated with the devices 200, 210 and coupled to the sensors can obtain a history of the user's biological indicators and can detect an anomaly in the user's biological indicators based on a difference between the historical biological indicators and a recent biological indicator. The processor can store the measurements of the prior biological indicators to obtain historical biological indicators or can obtain user's data from social media, doctor's visits, filled prescription(s), etc. to obtain historical biological indicators.

For example, the processor can access the user's information posted on social media, such as images and/or videos to obtain historical biological indicators of the user's appearance. If a recent image or video of the user shows a change in coloration of the user, such as a flushed appearance, the processor can detect an anomaly in the coloration of the user, which may indicate that the user has a fever. The processor can obtain an additional indicator, such as a temperature indicator through the watch 210, to confirm the anomaly.

In another example, the processor can gather information from an accelerometer sensor while the user is walking, to determine the user's balance. The accelerometer can be in the user's watch. The processor can send the information to a server to store the information as historical biological indicator information. The processor can record the user's present walk and can send the information about the user's walk to the server to detect any anomalies. The server can analyze the user's usual walk and the user's recently recorded walk to determine if there is an anomaly. If presently the user walks differently such as pausing more frequently and holding onto various objects for support, the server can determine that the user is having issues with balance, and it can notify the user, an authorized third party, and/or emergency responders.

In a third example, the sensor can be installed in a vehicle, such as a camera in the rearview mirror or the blind spot mirror, a microphone inside the vehicle to record the user's voice, a heartbeat monitor, a blood pressure monitor, and/or an oximeter in the steering wheel of the car. The sensors can measure the user state. For example, the camera in the rearview mirror can obtain a visual of the user and can detect signs of a stroke such as a drooping face. The camera can also track the eye movement and detect if the user is focusing on the road or has trouble with vision. The microphone in the vehicle can detect slurred speech. The processor connected to the sensors can determine based on the drooping face and the slurred speech that the user is having a stroke or seizure. Based on the determination, the vehicle can autonomously pull over or park to prevent an accident.

The vehicle can communicate the gathered information using the VTI protocol. VTI protocol is a communication model that allows vehicles to share information with the components that support a country's highway system. Such components include overhead radio frequency identification (RFID) readers and cameras, traffic lights, lane markers, streetlights, signage, and parking meters. VTI communication is typically wireless and bidirectional: data from infrastructure components can be delivered to the vehicle over an ad hoc network and vice versa. Similar to vehicle-to-vehicle (V2V) communication, VTI uses dedicated short-range communication (DSRC) frequencies to transfer data.

Figure 3:
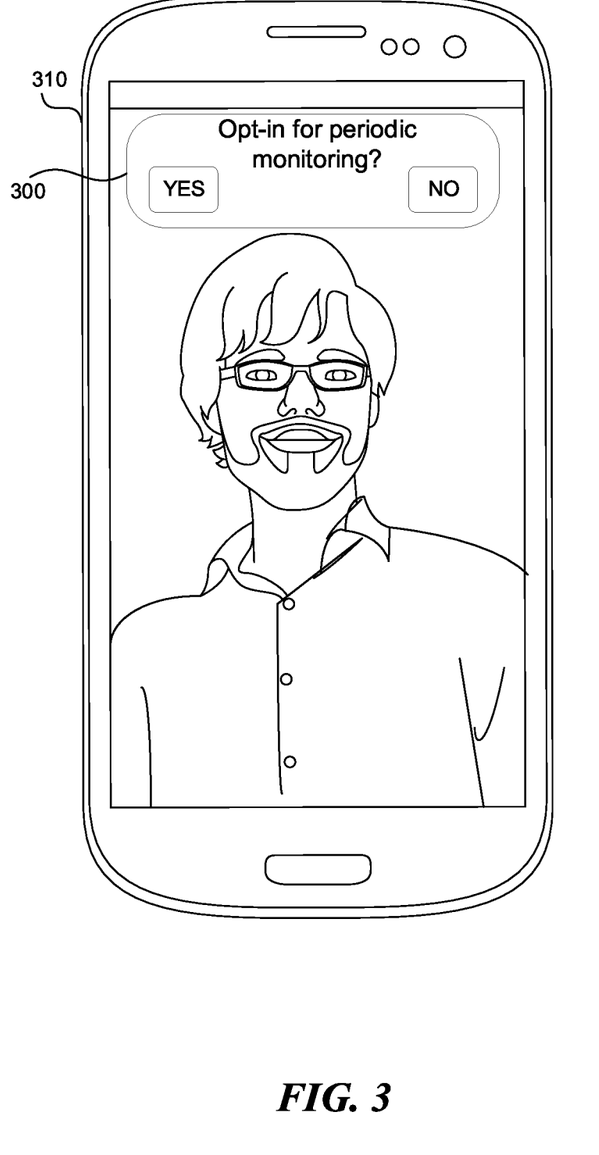
FIG. 3 shows a process to opt-in to use the system.

FIG. 3 shows a process to opt-in to use the system. To obtain nonpublic information of the user, such as records from doctors' visits, filled prescriptions, etc., the user or an authorized third party opts in to be monitored. For example, the user can opt-in to have a telemedicine visit to a doctor be recorded by the system.

The user can authorize a third party, such as a family member, to administer the user's account and/or to view notifications sent to the users, and/or anomalies detected by the system. The administration of the user's account can include opting in to various features of the system, such as allowing access to records of doctor's visits, allowing access to analyze images and audio of the user, and/or allowing unexpected measurements to be made. The history of biological indicators can be gathered and stored on a server under an anonymized ID, to preserve the user's privacy.

The system can occasionally record a measurement of the user, such as when the user looks at the mobile device. The system can ask the user to consent to the measurement, as shown in notification 300. If the user consents, the device 310 can record an image or video of the user for analysis and anomaly detection.

In another example, the system can occasionally record user speech and can ask for the user's opt-in through audio. If the user consents, the device 310 can record an audio of the user to detect if the user's speech has changed, such as if it has become slurred, or if the user is coughing, wheezing, sneezing, or the user's voice is raspy.

In a third example, if the user opts-in, the processor can use natural language processing to analyze the content of the user's voice calls and detect if the user is complaining of symptoms that can indicate disease. For example, the user can be complaining of a loss of smell and taste, fever, stomach issues, etc. If, based on historical biological indicators, the processor detects that the user does not normally complain of such symptoms, the processor can detect an anomaly that can be associated with symptoms of a disease such as COVID-19.

Figure 4:
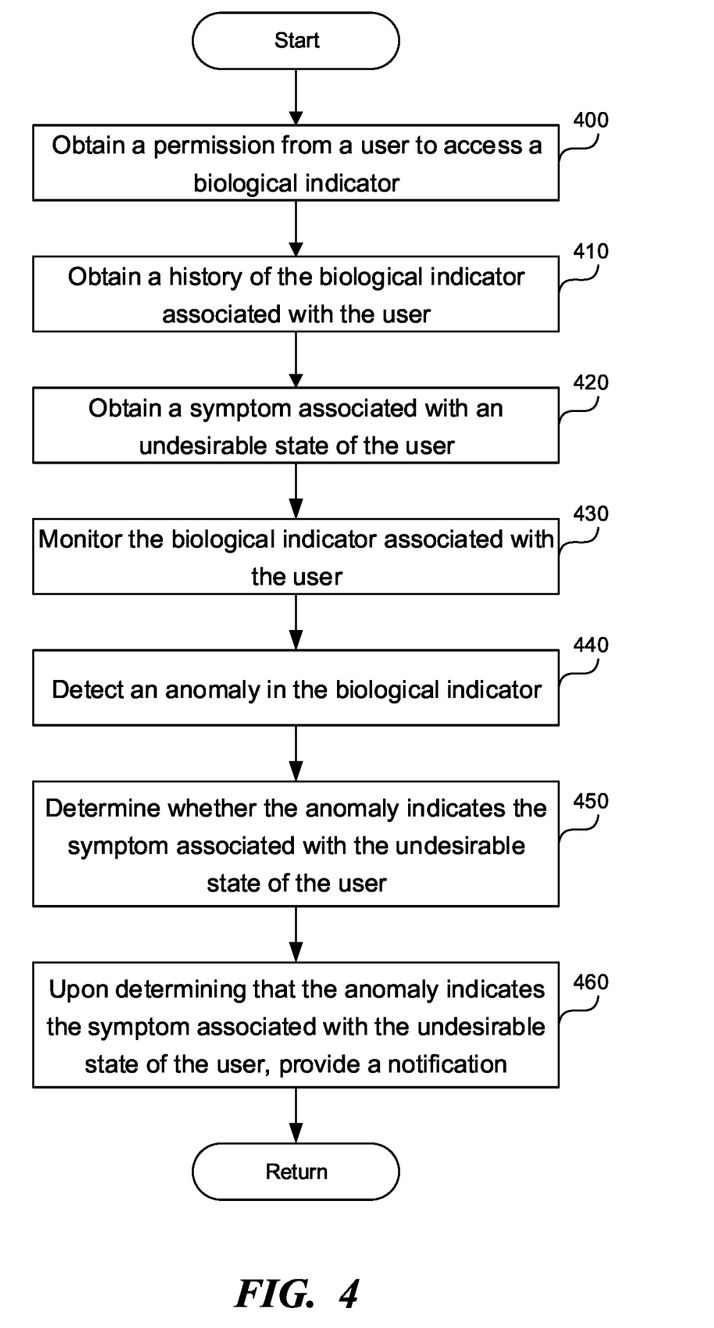
FIG. 4 is a flowchart that illustrates a process to monitor a user's biological indicators.

FIG. 4 is a flowchart that illustrates a process to monitor user's biological indicators. At block 400, a hardware or software processor executing instructions described in this application can obtain permission from a user to access a biological indicator, as shown in FIG. 3. The granted permission can include permission to obtain a current biological indicator as shown in FIG. 3, or permission to obtain a history of nonpublic biological indicators, such as records of previous doctor's visits.

At block 410, the processor can obtain a history of the biological indicator associated with the user. The biological indicator can include movement associated with the user, a voice associated with the user, an appearance associated with the user, urine analysis, breath analysis, blood pressure, fitness level, the weight associated with the user, skin complexion, etc. To obtain the history of the biological indicator, the processor can obtain an image, video, or a voice recording of the user posted on a social media platform.

At block 420, the processor can obtain a symptom associated with an undesirable state of the user. The undesirable state can include impaired functioning of the user due to disease, intoxication, vertigo, etc. The symptoms of the undesirable state can include affliction of the musculoskeletal system such as loss of balance, slurred speech, and an affliction of facial muscles. For example, the processor can obtain symptoms from a database of medical symptoms, such as a CDC database. The processor can obtain the symptoms of a stroke, which can include: sudden numbness or weakness in the face, arm, or leg, especially on one side of the body; sudden confusion, trouble speaking, slurred speech, or difficulty understanding speech; sudden trouble seeing in one or both eyes; sudden trouble walking, dizziness, loss of balance, or lack of coordination; sudden severe headache with no known cause.

At block 430, the processor can monitor the biological indicator associated with the user to obtain a recent biological indicator. For example, the processor can record an image of the user, the user's voice, the user's blood pressure, etc. The processor can monitor the biological indicator in real-time using a 5G telecommunication network or a higher generation telecommunication network. In other words, the processor can send the data from the sensors to a cloud server using the 5G telecommunication network or higher because the monitoring of the biological indicator requires a bandwidth of a 5G telecommunication network or higher. For example, obtaining and uploading the real-time video of the user requires a 5G network because of the high bandwidth demands of video. If the user is connected to the 5G network, the processor can obtain a real-time video of the user using a mobile device connected to the 5G telecommunication network. The processor can analyze the real-time video of the user to detect the anomaly in a visual appearance of the user, and upon detecting the anomaly, the processor can notify the user of the disease less than a second from obtaining the real-time video.

To reduce the bandwidth consumption even in the 5G telecommunication network or higher, the processor can compress the video prior to sending and/or can send the difference between the data that is already on the server and the currently collected data. The processor can encrypt the information prior to sending the information to the server.

To monitor the biological indicator, the processor can obtain permission from the user to record the biological indicator. The processor can determine a particular time to obtain the biological indicator from the user, where the particular time is not indicated to the user. The processor can obtain the biological indicator from the user, where the biological indicator is unaffected by the user anticipating the gathering of the biological indicator because the user was not aware of when the biological indicator would be collected from the user.

At block 440, the processor can detect an anomaly in the biological indicator by comparing the biological indicator with the history of the biological indicator. For example, by gathering real-time video, the processor can analyze the video to detect an anomaly, such as a droopy face, by comparing the current video of the user and the historical use of the user. The processor can compare the current voice of the user with the historical voice of the user to detect an anomaly such as a slurred speech. The processor can perform natural language processing on the voice to determine if the user is complaining of an anomaly such as a sudden headache or other symptoms. The processor can obtain orientation information for the user and can analyze whether the user is experiencing an anomaly such as the loss of balance.

The processor can compare information obtained currently from the user with historical information including static images from family gatherings, social media posts, and other publicly available sites. In anomaly detection, the processor can include medical history information such as a history of strokes, location information such as the user has recently visited a doctor, and/or prescription information, such as the user is on a high blood pressure medication. The processor can employ a cloud-based artificial intelligence (AI) model to detect the anomaly and to alert 911, emergency responders, family, and/or the impacted user. The AI model can perform an analysis of facial behaviors.

A "model," as used herein, refers to a construct that is trained using training data to make predictions or provide probabilities for new data items, whether or not the new data items were included in the training data. For example, training data for supervised learning can include items with various parameters and an assigned classification. A new data item can have parameters that a model can use to assign a classification to the new data item. As another example, a model can be a probability distribution resulting from the analysis of training data, such as a likelihood of a disease symptom occurring in a user based on an analysis of a large corpus of health history and biological indicators associated with the user. Examples of models include: neural networks, support vector machines, decision trees, Parzen windows, Bayes, clustering, reinforcement learning, probability distributions, decision trees, decision tree forests, and others. Models can be configured for various situations, data types, sources, and output formats.

In some implementations, the AI model can be a neural network with multiple input nodes that receive a measurement of a biological indicator, such as a video, an image of the user, or an accelerometer measurement of the user's balance. The input nodes can correspond to functions that receive the input and produce results. These results can be provided to one or more levels of intermediate nodes that each produce further results based on a combination of lower level node results. A weighting factor can be applied to the output of each node before the result is passed to the next layer node. At a final layer, ("the output layer,") one or more nodes can produce a value classifying the input that, once the model is trained, can be used as an indicator of an anomaly in the user's biological indicator. In some implementations, such neural networks, known as deep neural networks, can have multiple layers of intermediate nodes with different configurations, can be a combination of models that receive different parts of the input and/or input from other parts of the deep neural network, or are convolutions—partially using output from previous iterations of applying the model as further input to produce results for the current input.

A machine learning model can be trained with supervised learning, where the training data includes history of the biological indicator as input and a desired output, such as whether the biological indicator contains an anomaly. A representation of the biological indicator, such as a video, an image, an audio, or a series of measurements can be provided to the model. Output from the model can be compared to the desired output for that history of the biological indicator and, based on the comparison, the model can be modified, such as by changing weights between nodes of the neural network or parameters of the functions used at each node in the neural network (e.g., applying a loss function). After applying each of the histories of the biological indicators in the training data and modifying the model in this manner, the model can be trained to evaluate new measurements of a biological indicator.

At block 450, the processor can determine whether the anomaly indicates the symptom associated with the undesirable state of the user. For example, the processor can determine whether a loss of smell is associated with a disease, or whether a bruise on the shin is a symptom of an undesirable state.

At block 460, upon determining that the anomaly indicates the symptom associated with the undesirable state of the user, the processor can provide a notification to the user, to the authorized person, to 911, to the user's family, etc.

If the processor monitoring the user is connected to the server via a 4G network or lower generation network, the processor can reduce the frequency of monitoring the biological indicator associated with the user to predetermined times due to bandwidth limitations between the user and the system detecting the anomaly. For example, instead of continuously recording video, the processor can record occasional video snippets or images, and send those to the server via the 4G or lower generation network. The occasional video snippets can be recorded at a predetermined interval, such as every 15 minutes, every hour, every day, etc.

If the processor monitoring the user is connected to the server via a 5G network or higher generation network, the processor can continuously monitor the biological indicator associated with the user and can send the continuously monitored biological indicator over a 5G telecommunication network or later generation to the system configured to detect the anomaly. For example, if the user is driving, a camera in the rearview mirror or the dashboard can obtain a visual of the user, such as a video snippet. Based on the visual, the processor can determine an awareness state of the user and detect signs of impaired ability to drive such as the user being distracted, being intoxicated, or having a stroke, etc., and based on the awareness of the state of the user, the processor can determine how to control the vehicle. For example, if such an anomaly in the user's behavior is detected, the processor can warn the user to wake up, pay attention, pullover, etc. In addition, the processor can autonomously navigate the vehicle to a stop.

The processor can obtain information about an authorized third party from the user. The processor can share the anomaly or the biological indicator with the authorized third party. Similarly, the processor can send notifications to the authorized third party. The processor can also enable the authorized third party to provide instructions instead of the user. The authorized third party does not have to be physically co-located with the user. Instead, the authorized third party can access the user's information or act in the user's stead through a third-party portal. The system can gather data from IoT devices, watch and mobile phone, package it in one file and send to a health care provider's server where the system then applies the algorithm to determine whether to call the third-party.

Computer System

Figure 5:
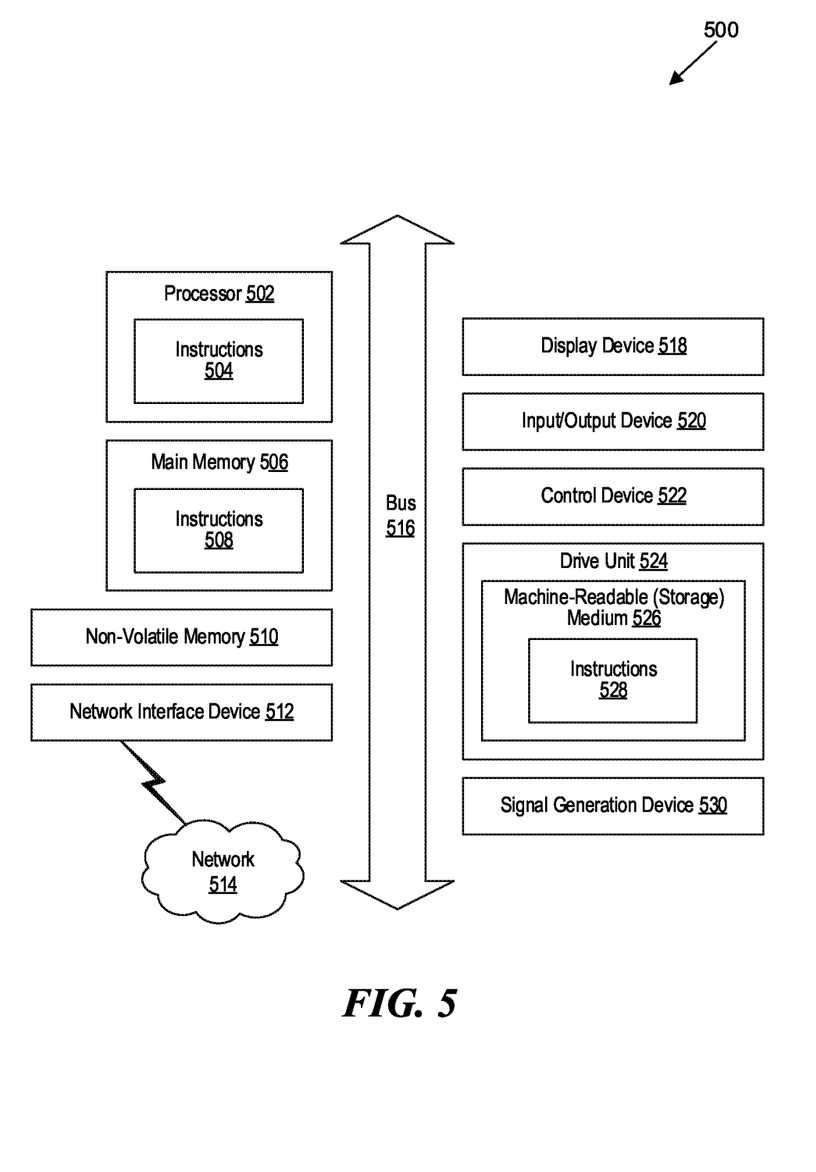
FIG. 5 is a block diagram that illustrates an example of a computer system in which at least some operations described herein can be implemented.

FIG. 5 is a block diagram that illustrates an example of a computer system 500 in which at least some operations described herein can be implemented. As shown, the computer system 500 can include: one or more processors 502, main memory 506, non-volatile memory 510, a network interface device 512, video display device 518, an input/output device 520, a control device 522 (e.g., keyboard and pointing device), a drive unit 524 that includes a storage medium 526, and a signal generation device 530 that are communicatively connected to a bus 516. The bus 516 represents one or more physical buses and/or point-to-point connections that are connected by appropriate bridges, adapters, or controllers. Various common components (e.g., cache memory) are omitted from FIG. 5 for brevity. Instead, the computer system 500 is intended to illustrate a hardware device on which components illustrated or described relative to the examples of the figures and any other components described in this specification can be implemented.

The processor 502 can execute the instructions described in this application, for example, instructions described in FIG. 4. The processor 502 can be connected to the various sensors described in this application. The processor 502 can be associated with the devices 200, 210 in FIG. 2. The main memory 502, the nonvolatile memory 510, and/or the drive unit 524 can store the instructions executed by the processor 502. The network 514 can be the telecommunication network used to communicate between devices 200, 210 and a server.

The computer system 500 can take any suitable physical form. For example, the computing system 500 can share a similar architecture as that of a server computer, personal computer (PC), tablet computer, mobile telephone, game console, music player, wearable electronic device, network-connected ("smart") device (e.g., a television or home assistant device), AR/VR systems (e.g., head-mounted display), or any electronic device capable of executing a set of instructions that specify action(s) to be taken by the computing system 500. In some implementation, the computer system 500 can be an embedded computer system, a system-on-chip (SOC), a single-board computer system (SBC) or a distributed system such as a mesh of computer systems, or it can include one or more cloud components in one or more networks. Where appropriate, one or more computer systems 500 can perform operations in real-time, near real-time, or in batch mode.

The network interface device 512 enables the computing system 500 to mediate data in a network 514 with an entity that is external to the computing system 500 through any communication protocol supported by the computing system 500 and the external entity. Examples of the network interface device 512 include a network adaptor card, a wireless network interface card, a router, an access point, a wireless router, a switch, a multilayer switch, a protocol converter, a gateway, a bridge, a bridge router, a hub, a digital media receiver, and/or a repeater, as well as all wireless elements noted herein.

The memory (e.g., main memory 506, non-volatile memory 510, machine-readable medium 526) can be local, remote, or distributed. Although shown as a single medium, the machine-readable medium 526 can include multiple media (e.g., a centralized/distributed database and/or associated caches and servers) that store one or more sets of instructions 528. The machine-readable (storage) medium 526 can include any medium that is capable of storing, encoding, or carrying a set of instructions for execution by the computing system 500. The machine-readable medium 526 can be non-transitory or comprise a non-transitory device. In this context, a non-transitory storage medium can include a device that is tangible, meaning that the device has a concrete physical form, although the device can change its physical state. Thus, for example, non-transitory refers to a device remaining tangible despite this change in state.

Although implementations have been described in the context of fully functioning computing devices, the various examples are capable of being distributed as a program product in a variety of forms. Examples of machine-readable storage media, machine-readable media, or computer-readable media include recordable-type media such as volatile and non-volatile memory devices 510, removable flash memory, hard disk drives, optical discs, and transmission-type media such as digital and analog communication links.

In general, the routines executed to implement examples herein can be implemented as part of an operating system or a specific application, component, program, object, module, or sequence of instructions (collectively referred to as "computer programs"). The computer programs typically comprise one or more instructions (e.g., instructions 504, 508, 528) set at various times in various memory and storage devices in computing device(s). When read and executed by the processor 502, the instruction(s) cause the computing system 500 to perform operations to execute elements involving the various aspects of the disclosure.

Remarks

The terms "example," "embodiment," and "implementation" are used interchangeably. For example, references to "one example" or "an example" in the disclosure can be, but not necessarily are, references to the same implementation; and, such references mean at least one of the implementations. The appearances of the phrase "in one example" are not necessarily all referring to the same example, nor are separate or alternative examples mutually exclusive of other examples. A feature, structure, or characteristic described in connection with an example can be included in another example of the disclosure. Moreover, various features are described which can be exhibited by some examples and not by others. Similarly, various requirements are described which can be requirements for some examples but no other examples.

The terminology used herein should be interpreted in its broadest reasonable manner, even though it is being used in conjunction with certain specific examples of the invention. The terms used in the disclosure generally have their ordinary meanings in the relevant technical art, within the context of the disclosure, and in the specific context where each term is used. A recital of alternative language or synonyms does not exclude the use of other synonyms. Special significance should not be placed upon whether or not a term is elaborated or discussed herein. The use of highlighting has no influence on the scope and meaning of a term. Further, it will be appreciated that the same thing can be said in more than one way.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import can refer to this application as a whole and not to any particular portions of this application. Where context permits, words in the above Detailed Description using the singular or plural number may also include the plural or singular number respectively. The word "or" in reference to a list of two or more items covers all of the following interpretations of the word: any of the items in the list, all of the items in the list, and any combination of the items in the list. The term "module" refers broadly to software components, firmware components, and/or hardware components.

While specific examples of technology are described above for illustrative purposes, various equivalent modifications are possible within the scope of the invention, as those skilled in the relevant art will recognize. For example, while processes or blocks are presented in a given order, alternative implementations can perform routines having steps, or employ systems having blocks, in a different order, and some processes or blocks may be deleted, moved, added, subdivided, combined, and/or modified to provide alternative or sub-combinations. Each of these processes or blocks can be implemented in a variety of different ways. Also, while processes or blocks are at times shown as being performed in series, these processes or blocks can instead be performed or implemented in parallel or can be performed at different times. Further, any specific numbers noted herein are only examples such that alternative implementations can employ differing values or ranges.

Details of the disclosed implementations can vary considerably in specific implementations while still being encompassed by the disclosed teachings. As noted above, particular terminology used when describing features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed herein, unless the above Detailed Description explicitly defines such terms. Accordingly, the actual scope of the invention encompasses not only the disclosed examples, but also all equivalent ways of practicing or implementing the invention under the claims. Some alternative implementations can include additional elements to those implementations described above or include fewer elements.

Any patents and applications and other references noted above, and any that may be listed in accompanying filing papers, are incorporated herein by reference in their entireties, except for any subject matter disclaimers or disavowals, and except to the extent that the incorporated material is inconsistent with the express disclosure herein, in which case the language in this disclosure controls. Aspects of the invention can be modified to employ the systems, functions, and concepts of the various references described above to provide yet further implementations of the invention.

To reduce the number of claims, certain implementations are presented below in certain claim forms, but the applicant contemplates various aspects of an invention in other forms. For example, aspects of a claim can be recited in a means-plus-function form or in other forms, such as being embodied in a computer-readable medium. A claim intended to be interpreted as a mean-plus-function claim will use the words "means for." However, the use of the term "for" in any other context is not intended to invoke a similar interpretation. The applicant reserves the right to pursue such additional claim forms in either this application or in a continuing application.

I claim:

1. At least one computer-readable storage medium, excluding transitory signals, and carrying instructions, which, when executed by at least one data processor of a system, cause the system to:
    obtain a permission from a user to access a biological indicator;
    obtain a history of the biological indicator associated with the user,
        wherein the biological indicator includes user's voice, and an appearance associated with the user;
    obtain multiple symptoms associated with a stroke,
        wherein the multiple symptoms include a loss of balance, a slurred speech, and an affliction of facial muscles;
    obtain, using a 5G telecommunication network, the biological indicator associated with the user,
        wherein the obtaining occurs during a call without indicating to the user a particular time when the biological indicator is obtained;
    detect an anomaly in the biological indicator by comparing the biological indicator with the history of the biological indicator, wherein instructions to detect the anomaly include instructions to:
        compare the user's voice to a history of the user's voice;
        determine whether the user's voice is slurred compared to the history of the user's voice,
        upon determining that the user's voice is slurred compared to the history of the user's voice, detect the anomaly;
    determine whether the anomaly indicates at least one symptom among the multiple symptoms associated with the stroke; and
    upon determining that the anomaly indicates the at least one symptom among the multiple symptoms associated with the stroke, provide a notification, via the 5G telecommunication network and to a third party, that the user is possibly experiencing the stroke.

2. The at least one computer-readable storage medium of claim 1, further comprising instructions to: obtain a real-time video of the user using a mobile device connected to the 5G telecommunication network; analyze the real-time video of the user to detect the anomaly in a visual appearance of the user; and upon detecting the anomaly, notify the user of the stroke less than a second from obtaining the real-time video.

3. The at least one computer-readable storage medium of claim claim 1, further comprising instructions to: obtain from a camera installed in a vehicle a visual of the user; based on the visual, determine an awareness state of the user; and based on the awareness state of the user, determine how to automatically control the vehicle.

4. The at least one computer-readable storage medium of claim claim 1, wherein the instructions to obtain the biological indicator require a bandwidth of a 5G telecommunication network.

5. A system comprising:
    at least one hardware processor; and
    at least one non-transitory memory coupled to the at least one hardware processor and storing instructions, which, when executed by the at least one hardware processor, cause the system to:
        obtain a permission from a user to access a biological indicator;
        obtain data related to the biological indicator associated with the user,
            wherein the biological indicator includes movement associated with the user, a voice associated with the user, or an appearance associated with the user;
        obtain a symptom associated with an undesirable state of the user,
            wherein the symptom includes affliction of a musculoskeletal system;
        obtain the biological indicator associated with the user,
            wherein the obtaining occurs during a call without indicating to the user a particular time when the biological indicator is obtained;
        detect an anomaly in the biological indicator by comparing the biological indicator with the data related to the biological indicator, wherein instructions to detect the anomaly include instructions to:
            compare the user's voice to the data related to the biological indicator including a history of the user's voice;
            determine whether the user's voice is slurred compared to the history of the user's voice,
            upon determining that the user's voice is slurred compared to the history of the user's voice, detect the anomaly;
        determine whether the anomaly indicates the undesirable state of the user; and
        upon determining that the anomaly indicates the undesirable state of the user, provide a notification.

6. The system of claim 5, further caused to: reduce a frequency of monitoring the biological indicator associated with the user to predetermined times due to bandwidth limitations between a UE and the system detecting the anomaly.

7. The system of claim 5, further caused to: continuously monitor the biological indicator associated with the user; and send the continuously monitored biological indicator over a 5G telecommunication network to the system configured to detect the anomaly.

8. The system of claim 5, the instructions to monitor further causing the system to: obtain a real-time video of the user using a UE connected to a 5G telecommunication network; analyze the real-time video of the user to detect the anomaly in a visual appearance of the user; and upon detecting the anomaly, notify the user of the undesirable state less than a second from obtaining the real-time video.

9. The system of claim 5, further caused to: obtain from a camera installed in a vehicle a visual of the user; based on the visual, determine an awareness state of the user; and based on the awareness state of the user, determine how to control the vehicle.

10. The system of claim 5, further caused to: obtain information about an authorized third party from the user; and share the anomaly or the biological indicator with the authorized third party.

11. The system of claim 5, further caused to: obtain information about an authorized third party from the user; and enable the authorized third party to provide instructions instead of the user.

12. The system of claim 5, further caused to: determine a particular time to obtain the biological indicator from the user, wherein the particular time is not indicated to the user; and obtain the biological indicator from the user.

13. A method comprising:
receiving a permission from a user to access a biological indicator;
obtaining a history of the biological indicator associated with the user,
wherein the biological indicator includes movement associated with the user, a voice associated with the user, or an appearance associated with the user;
obtaining a symptom associated with an undesirable state of the user,
wherein the symptom includes affliction of a musculoskeletal system;
monitoring the biological indicator associated with the user,
wherein the monitoring occurs during a call without indicating to the user a particular time when the biological indicator is obtained;
detecting an anomaly in the biological indicator by comparing the biological indicator with the history of the biological indicator, wherein detecting the anomaly includes:
comparing the user's voice to a history of the user's voice;
determining whether the user's voice is slurred compared to the history of the user's voice,
upon determining that the user's voice is slurred compared to the history of the user's voice, detecting the anomaly;
determining whether the anomaly indicates the symptom associated with the undesirable state of the user; and
upon determining that the anomaly indicates the symptom associated with the undesirable state of the user, providing a notification.

14. The method of claim 13, further comprising: determining that a UE is connected to a 4G telecommunication network or lower generation telecommunication network; and reducing a frequency of monitoring the biological indicator associated with the user to predetermined times due to bandwidth limitations between the UE and a processor detecting the anomaly.

15. The method of claim 13, further comprising: continuously monitoring the biological indicator associated with the user; and sending the continuously monitored biological indicator over a 5G telecommunication network to a processor configured to detect the anomaly.

16. The method of claim 13, the monitoring further comprising: obtaining a real-time video of the user using a UE connected to a 5G telecommunication network; analyzing the real-time video of the user to detect the anomaly in a visual appearance of the user; and upon detecting the anomaly, notifying the user of the undesirable state less than a second from obtaining the real-time video.

17. The method of claim 13, further comprising: obtaining from a camera installed in a vehicle a visual of the user; based on the visual, determining an awareness state of the user; and based on the awareness state of the user, determining how to control the vehicle.

18. The method of claim 13, further comprising: obtaining information about an authorized third party from the user; and sharing the anomaly or the biological indicator with the authorized third party.

19. The method of claim 13, the obtaining the history of the biological indicator associated with the user further comprising: obtaining an image, a video, or a voice recording of the user posted on a social media platform.

20. The method of claim 13, the monitoring further comprising: determining a particular time to obtain the biological indicator from the user, wherein the particular time is not indicated to the user; and obtaining the biological indicator from the user.

* * * * *